(12) United States Patent
Saito et al.

(10) Patent No.: US 9,968,677 B2
(45) Date of Patent: May 15, 2018

(54) STABILIZED PROTEIN-CONTAINING FORMULATIONS

(75) Inventors: Akihiko Saito, Kita-ku (JP); Eiichi Miyauchi, Chuo-ku (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days. days.

(21) Appl. No.: 12/415,400

(22) Filed: Mar. 31, 2009

(65) Prior Publication Data
US 2009/0264629 A1    Oct. 22, 2009

Related U.S. Application Data

(62) Division of application No. 10/547,366, filed as application No. PCT/JP2004/002429 on Feb. 27, 2004.

(30) Foreign Application Priority Data

Feb. 28, 2003 (JP) ................. 2003-053379

(51) Int. Cl.
| | | |
|---|---|---|
| A61K 38/19 | (2006.01) | |
| A61K 9/08 | (2006.01) | |
| A61K 47/10 | (2017.01) | |
| C07K 14/535 | (2006.01) | |
| A61K 39/395 | (2006.01) | |
| A61K 9/00 | (2006.01) | |
| A61K 38/29 | (2006.01) | |
| C07K 16/36 | (2006.01) | |

(52) U.S. Cl.
CPC ...... *A61K 39/39591* (2013.01); *A61K 9/0019* (2013.01); *A61K 9/08* (2013.01); *A61K 38/193* (2013.01); *A61K 38/29* (2013.01); *A61K 47/10* (2013.01); *C07K 14/535* (2013.01); *C07K 16/36* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 4,839,341 A | * | 6/1989 | Massey et al. | 514/6.4 |
| 4,902,500 A | | 2/1990 | Jansen et al. | |
| 5,358,708 A | * | 10/1994 | Patel | A61K 38/193 424/85.1 |
| 5,696,090 A | * | 12/1997 | McGregor et al. | 514/21.2 |
| 5,744,163 A | | 4/1998 | Kim et al. | |
| 5,811,096 A | | 9/1998 | Aleman et al. | |
| 6,004,968 A | | 12/1999 | Casey et al. | |
| 6,015,568 A | | 1/2000 | Segot et al. | |
| 6,171,586 B1 | * | 1/2001 | Lam et al. | 424/130.1 |
| 6,238,664 B1 | | 5/2001 | Hellerbrand et al. | |
| 6,267,958 B1 | | 7/2001 | Andya et al. | |
| 6,342,477 B1 | | 1/2002 | Tamura et al. | |
| 6,677,436 B1 | | 1/2004 | Sato et al. | |
| 6,776,983 B1 | * | 8/2004 | Sumida | A61K 38/193 424/85.1 |
| 2002/0058626 A1 | | 5/2002 | Tamura et al. | |
| 2003/0059470 A1 | | 3/2003 | Muller | |
| 2004/0044187 A1 | | 3/2004 | Sato et al. | |

FOREIGN PATENT DOCUMENTS

| | | |
|---|---|---|
| CA | 2234724 | 10/1996 |
| CA | 2272245 A1 | 5/1998 |
| CA | 2466034 | 5/2003 |
| EP | 0 272 703 | 6/1988 |
| EP | 1 172 114 A2 | 1/2002 |
| EP | 1197221 A1 | 4/2002 |
| EP | 1 222 854 A1 | 7/2002 |
| EP | 1 297 842 A1 | 4/2003 |
| GB | 2193631 | 2/1988 |
| JP | 63-146828 | 8/1988 |
| JP | 63267292 | 11/1988 |
| JP | 1-168624 | 7/1989 |
| JP | H6-172199 | 12/1994 |
| JP | 7-165587 | 6/1995 |
| JP | 9-25242 A | 1/1997 |
| JP | 9-174348 | 7/1997 |
| JP | 9-301887 | 11/1997 |
| JP | 11-515002 | 12/1999 |
| JP | 2000-247903 | 9/2000 |
| JP | 2001-501974 | 2/2001 |
| JP | 2001-503781 | 3/2001 |
| JP | 2002-371009 | * 12/2002 |
| JP | 2003-342193 | 12/2003 |
| WO | WO 94/03157 | 2/1994 |
| WO | 9503783 | 2/1995 |
| WO | WO 00/23098 | 10/1998 |
| WO | WO 99/16421 | 4/1999 |
| WO | WO 99/17743 | 4/1999 |
| WO | WO99/44630 | * 9/1999 |
| WO | WO 99/44631 A1 | 9/1999 |
| WO | WO 99/45953 A1 | 9/1999 |
| WO | WO 99/51743 | 10/1999 |
| WO | WO 99/66044 | 12/1999 |
| WO | WO 00/10526 | 3/2000 |
| WO | WO 00/23101 | 4/2000 |
| WO | WO 01/24826 A1 | 9/2000 |
| WO | WO 00/71149 A2 | 11/2000 |
| WO | WO 01/58474 A2 | 8/2001 |
| WO | WO 02/02136 A1 | 1/2002 |
| WO | WO 02/09667 A2 | 2/2002 |
| WO | WO 02/17932 A1 | 3/2002 |
| WO | 01/70984 | 9/2011 |

OTHER PUBLICATIONS

Benmimoun et al., Development, 2012, vol. 139(10):1713-1717.*
English translation of JP 2002-371009 (Pub. Date: Dec. 26, 2002) (machine-generated).*
Presta et al., Throm. Haemost., 2001, 85(3); 379-389.
Takahashi, O., Food Chem. Toxicol., 1995, 33(2):121-128.
(Continued)

*Primary Examiner* — Xiaozhen Xie
(74) *Attorney, Agent, or Firm* — Browdy and Neimark, P.L.L.C.

(57) ABSTRACT

A method for maintaining the biological activity in a protein formulation without adding an antioxidant and for inhibiting the formation of insoluble particles, comprising adding to the protein formulation a poloxamer as a surfactant.

5 Claims, 5 Drawing Sheets

(56) References Cited

OTHER PUBLICATIONS

Herman, et al., "Characterization of Neupogen® (Filgrastim), a Recombinant Human Granulocyte Stimulating Factor", in Pearlman and Wang, Formulation, Characterization, and Stability of Protein Drugs:Case Histories, Chapter 7, pp. 303-328 (Springer 1996) (only pp. 324-325 provided).
Hovorka, et al, Oxidative Degradation of Pharmaceuticals: Theory, Mechanisms and Inhibition, Journal of Pharmaceutical Sciences, vol. 90, No. 3, pp. 253-269, Mar. 2001.
Knepp, et al., Identification of Antioxidants for Prevention of Peroxide-Mediated Oxidation of Recombinant Human ciliary Neurotrophic Factor and Recombinant Human Nerve Growth Factor, PDA Jouranl of Pharmaceutical Science and Technology, vol. 50, No. 3, pp. 163-171, May-Jun. 1996.
Supplementary European Search Report from EP 04 71 5529, dated Sep. 20, 2011.
EPO Office Action from 04715529.6-2112, dated May 16, 2012.
Office Action dated Jan. 9, 2014 for Canadian Application No. 2,517,310.
Katakam, et al., Use of Poloxamer Polymers to Stabilize Recombinant Human Growth Hormone Against Various Processing Stresses, Pharmaceutical Development and Technology, 1997, pp. 143-149, vol. 2(2).
Ha, et al., Peroxide Formation in Polysorbate 80 and Protein Stability, Journal of Pharmaceutical Sciences, Oct. 2002, pp. 2252-2264, vol. 91, No. 10.

\* cited by examiner

STABILIZED PROTEIN-CONTAINING FORMULATIONS

TECHNICAL FIELD

The present invention relates to stable protein-containing formulations. More specifically, the present invention relates to stable protein-containing formulations containing a poloxamer as a surfactant.

BACKGROUND ART

With the development of genetic engineering technology, it has become possible to use physiologically active proteins such as antibodies, enzymes, hormones and cytokines as pharmaceutical products. To supply them in stable amounts with high quality, it is necessary to establish preparation conditions and storage conditions under which the structure and activity can be maintained.

Generally, a problem encountered during storage of proteins is a deterioration phenomenon such as the formation of insoluble aggregates and must be prevented.

For example, antibodies such as immunoglobulins, monoclonal antibodies and humanized antibodies are unstable proteins liable to physical or chemical changes such as association or aggregation under stresses of filtration, concentration and heat during purification and formulation processes as well as stresses of heat, light and transportation during storage of stock solutions or formulations.

When antibodies are to be obtained by genetic engineering techniques, antibody-producing cells are cultured in bulk and purified to give an antibody-containing solution, which is then stored frozen and thawed before formulation. However, the antibody content remaining in such a solution decreased as antibody dimers or insoluble particles or foreign insoluble matters were formed during repeated freeze/thaw cycles or antibodies were degraded to form degradation products during long-term storage.

In order to inhibit the formation of such foreign insoluble matters and to obtain stable protein-containing formulations, the use of surfactants is indispensable, and especially, such surfactants as polysorbates 20 and 80 have been widely used. In the case of readily oxidizable protein formulations, however, antioxidants such as L-methionine had to be included in addition to polysorbate 80 (JPA No. 2000-247903, J. Pharm. Sci. 90:3 (2001)) because polysorbate 80 tends to oxidize proteins (PDA J. Pharm. Sci. Technol. 50:3 (1996); Formulation, Characterization, and Stability of Protein Drugs. Plenum Press, New Yolk, (1996)), thereby lowering the biological activity of antibody formulations. The addition of antioxidants required complex operations such as strict determination of the specifications and amounts of the antioxidants.

Thus, it would be desirable to provide a surfactant capable of inhibiting the oxidation of proteins without adding antioxidants and capable of inhibiting the formation of foreign insoluble matters in protein formulations. Lyophilized formulations can inhibit the oxidation of proteins (for example, JPA No. 2000-247903), but there are great demands for convenient solution formulations eliminating the reconstitution step and it would also be desirable to provide protein-containing formulations that are stable even as solution formulations.

An object of the present invention is to find a surfactant capable of inhibiting the oxidation of proteins without adding antioxidants to maintain the biological activity of the proteins and also capable of inhibiting the formation of foreign insoluble matters in protein formulations and to provide a stabilized protein-containing formulation containing said surfactant.

DISCLOSURE OF THE INVENTION

As a result of careful studies to achieve the above object, we accomplished the present invention on the basis of the finding that the biological activity of proteins can be maintained without causing oxidation of the proteins in the absence of antioxidants and the formation of foreign insoluble matters can be inhibited in protein-containing formulations by adding a poloxamer as a surfactant.

Accordingly, the present invention provides:

(1) a protein formulation containing a poloxamer as a surfactant;

(2) the protein formulation as defined in (1) above wherein the poloxamer is poloxamer 188;

(3) the protein formulation as defined in (1) or (2) above, which is a solution formulation;

(4) the protein formulation as defined in any one of (1) to (3) above wherein the protein is an immunoglobulin;

(5) the protein formulation as defined in (4) above wherein the immunoglobulin is a humanized antibody;

(6) the protein formulation as defined in (4) above wherein the immunoglobulin is an anti-tissue factor antibody;

(7) the protein formulation as defined in (6) above wherein the anti-tissue factor antibody is a humanized anti-tissue factor antibody;

(8) the protein formulation as defined in any one of (1) to (9) above, which is free from antioxidant as an additive;

(9) a method for maintaining the biological activity in a protein formulation without adding an antioxidant and for inhibiting the formation of foreign insoluble matters by adding a poloxamer as a surfactant;

(10) the protein formulation as defined in any one of (1) to (3) above wherein the protein is granulocyte colony-stimulating factor; and

(11) the protein formulation as defined in any one of (1) to (3) above wherein the protein is parathyroid hormone.

THE MOST PREFERRED EMBODIMENTS OF THE INVENTION

Figure 1:
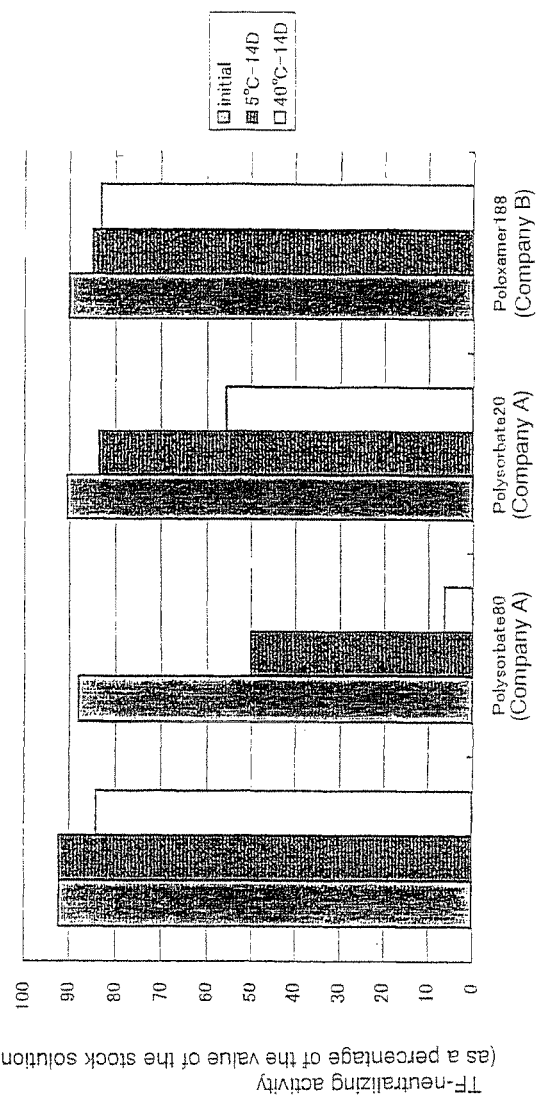
FIG. 1 shows changes in biological activity over time in anti-human tissue factor antibody solution formulations containing various surfactants.

As used herein, "protein-containing formulation" means a formulation containing a protein, preferably a physiologically active protein as an active ingredient and prepared for administration to animals such as humans, including both lyophilized formulations and solution formulations.

Proteins used in formulations of the present invention include, but not limited to, antibodies, enzymes, cytokines and hormones. Specifically, they include, but not limited to, hematopoietic factors such as granulocyte colony-stimulating factor (G-CSF), granulocyte macrophage colony-stimulating factor (GM-CSF), erythropoietin (EPO) and thrombopoietin; cytokines such as interferons, IL-1 and IL-6; immunoglobulins; monoclonal antibodies; humanized antibodies; tissue plasminogen activator (TPA); urokinase; serum albumin; blood coagulation factor VIII; leptin; insulin; and stem cell growth factor (SCF). Among those proteins, hematopoietic factors such as G-CSF and EPO, parathyroid hormone (PTH) and immunoglobulins are preferred, especially antibodies. Among antibodies, anti-tissue factor antibodies are especially preferred.

Proteins used in formulations of the present invention have substantially the same biological activities as those of physiologically active proteins of mammals, especially humans, and include those derived from natural sources and preferably those genetically engineered. Genetically engineered proteins may have the same amino acid sequences as those of natural proteins or may contain deletion, substitution or addition of one or more amino acids in said amino acid sequences while maintaining said biological activities. Physiologically active proteins also include those chemically modified with PEG or the like.

Proteins having a sugar chain are especially preferred. The sugar chain may be derived from any source, but preferably those added to mammalian cells. Mammalian cells include, for example, Chinese hamster ovary (CHO) cells, BHK cells, COS cells, human-derived cells, etc., among which CHO cells are most preferred.

When the protein is EPO, EPO may be prepared by any process, e.g. it may be extracted from human urine and isolated and purified by various techniques or may be produced by genetic engineering techniques (for example, JPA No. SHO 61-12288) in Chinese hamster ovary (CHO) cells, BHK cells, COS cells, human-derived cells or the like and then extracted and isolated and purified by various techniques. EPO chemically modified with PEG or the like is also included (see International Patent Application Publication No. WO90/12874). EPO having no sugar chain and chemically modified with PEG or the like is also included. EPO analogs are also included, in which EPO has been modified to increase the number of one or more glycosylation sites at the N-linked carbohydrate chain binding site or O-linked carbohydrate binding site in the amino acid sequence of EPO (for example, see JPA No. HEI 8-151398 and JPA No. HEI 8-506023). Moreover, the amount of sugar chains may be increased by increasing the content of sialic acid or the like without changing the number of sugar chain-binding sites.

When the protein is G-CSF, any high-purity human G-CSF can be used. G-CSF in the present invention may be prepared by any process, e.g., they may be extracted from cultures of a human tumor cell line and isolated and purified by various techniques or may be produced by genetic engineering techniques in bacterial cells such as *E. coli*; yeast cells; animal culture cells such as Chinese hamster ovary (CHO), C127 or COS cells and then extracted and isolated and purified by various techniques. G-CSF is preferably produced by genetic recombination in *E. coli*, yeast or CHO cells, most preferably by genetic recombination in CHO cells. G-CSF chemically modified with PEG or the like is also included (see International Patent Application Publication No. WO90/12874).

When the protein is an antibody, the antibody is not specifically limited so far as it binds to a desired antigen, and mouse antibodies, rat antibodies, rabbit antibodies, sheep antibodies, chimeric antibodies, humanized antibodies, human antibodies and the like can be used as appropriate. The antibodies may be polyclonal or monoclonal, but preferably monoclonal because homogeneous antibodies can be stably produced. Polyclonal and monoclonal antibodies can be prepared by processes well known to those skilled in the art.

Hybridomas producing monoclonal antibodies can be basically constructed by known techniques as follows. A desired antigen or a cell expressing a desired antigen is used as an immunizing antigen to immunize host cells according to a standard immunization technique, and the resulting immunized cells are fused to known parent cells by a standard cell fusion technique, and then the fused cells are screened for monoclonal antibody-producing cells (hybridomas) by a standard screening method. Construction of hybridomas can be performed according to the method of e.g. Milstein et al. (Kohler. G. and Milstein, C., Methods Enzymol. (1981) 73: 3-46). If the antigen has low immunogenicity, it can be bound to an immunogenic macromolecule such as albumin and used for immunization.

Recombinant antibodies can be used, which are produced by transforming a host with a suitable vector containing an antibody gene cloned from a hybridoma using genetic engineering techniques (see e.g. Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA sequences for the variable regions (V regions) of an antibody are synthesized from mRNA of a hybridoma using a reverse transcriptase. Once DNA sequences encoding the V regions of the antibody of interest have been obtained, they may be linked to the DNA sequences encoding the constant regions (C regions) of the antibody of interest and integrated into an expression vector. Alternatively, the DNA sequences encoding the V regions of the antibody may be integrated into an expression vector containing the DNA sequences for the C regions of the antibody. They are integrated into the expression vector in such a manner that they can be expressed under the control of regulatory regions such as enhancers and promoters. Then, a host cell can be transformed with this expression vector to express the antibody.

In the present invention, recombinant antibodies, i.e. antibodies artificially modified to reduce antigenicity in humans or to attain other purposes, such as chimeric antibodies and humanized antibodies can be used. These modified antibodies can be prepared by known processes. Chimeric antibodies consist of the heavy and light chain variable regions of an antibody from a non-human mammal such as a mouse and the heavy and light chain constant regions of a human antibody and can be obtained by linking the DNA sequences encoding the variable regions of the mouse antibody to the DNA sequences for the constant regions of the human antibody and transforming a host with an expression vector containing the linked sequences to allow it to produce a chimeric antibody.

Humanized antibodies are also called reshaped human antibodies and obtained by grafting the complementarity-determining regions (CDRs) of an antibody from a non-human mammal such as a mouse into the complementarity-determining regions of a human antibody and typical gene recombination techniques for preparing them are also known. Specifically, DNA sequences designed to link the CDRs of a mouse antibody to the framework regions (FRs) of a human antibody are synthesized by PCR from several oligonucleotides prepared to have terminal overlapping regions. The resulting DNA sequences are linked to the DNA sequences encoding the constant regions of the human antibody and then integrated into an expression vector, which is transformed into a host to allow it to produce a reshaped antibody (see European Patent Application Publication No. EP 239400, International Patent Application Publication No. WO 96/02576). The FRs of the human antibody linked by the CDRs are selected in such a manner that the complementarity-determining regions form an appropriate antigen-binding site. If necessary, reshaped humanized antibodies may have some amino acid changes in the framework regions of the variable regions so that the complementarity-determining regions form an appropriate antigen-binding site (Sato, K. et al., Cancer Res. (1993) 53, 851-856).

Methods for obtaining human antibodies are also known. For example, a desired human antibody having a binding activity for a desired antigen can be obtained by in vitro immunizing human lymphocytes with the desired antigen or a cell expressing the desired antigen and fusing the immunized lymphocytes to human myeloma cells such as U266 (see JPB No. HEI 1-59878). A desired human antibody can also be obtained by immunizing a transgenic animal having all human antibody gene repertoires with an antigen (see International Patent Application Publications Nos. WO 93/12227, WO 92/03918, WO 94/02602, WO 94/25585, WO 96/34096, WO 96/33735). Methods for obtaining a human antibody by panning using a human antibody library are also known. For example, phages binding to an antigen can be selected by expressing the variable regions of a human antibody as single chain antibody fragments (scFv) on phage surfaces by a phage display method. The DNA sequences encoding the variable regions of the human antibody binding to the antigen can be determined by analyzing the genes of the selected phages. A whole human antibody can be obtained by preparing a suitable expression vector on the basis of the determined DNA sequences of the scFv fragments binding to the antigen. These methods have already been well known from WO 92/01047, WO 92/20791, WO 93/06213, WO 93/11236, WO 93/19172, WO 95/01438, WO 95/15388.

When an antibody is to be prepared by transforming a preliminarily isolated antibody gene into a suitable host, the suitable host can be used in combination with an expression vector. Suitable eukaryotic cells used as hosts include animal cells, plant cells and fungal cells. Known animal cells include (1) mammalian cells such as CHO, COS, myeloma, BHK (baby hamster kidney), HeLa and Vero cells; (2) amphibian cells such as *Xenopus oocytes*; or (3) insect sells such as sf9, sf21 and Tn5. Known plant cells include cells of *Nicotiana* such as *Nicotiana tabacum*, which can be used as callus cultures. Known fungal cells include yeasts such as *Saccharomyces* spp., e.g. *Saccharomyces serevisiae* and filamentous fungi such as *Aspergillus* spp., e.g. *Aspergillus niger*. Prokaryotic cells can be used as producing systems using bacterial cells. Known bacterial cells include *E. coli* and *Bacillus subtilis*. Antibodies can be obtained by transforming these cells with an antibody gene of interest and culturing the transformed cells in vitro.

Antibodies contained in stabilized formulations of the present invention include, but not limited to, anti-IL-6 receptor antibodies, anti-HM1.24 antigen monoclonal antibodies, anti-parathyroid hormone related peptide antibodies (anti-PTHrP antibodies), anti-tissue factor antibodies, etc.

Preferred reshaped humanized antibodies for use in the present invention include humanized anti-IL-6 receptor antibodies (hPM-1) (see International Patent Application Publication No. WO92-19759), humanized anti-HM1.24 antigen monoclonal antibodies (see International Patent Application Publication No. WO98-14580) and humanized anti-parathyroid hormone related peptide antibodies (anti-PTHrP antibodies) (see International Patent Application Publication No. WO98-13388).

We prepared human/mouse chimeric antibodies consisting of the variable regions (V regions) of a mouse monoclonal antibody against human tissue factor and the constant regions (C regions) of a human antibody as well as humanized antibodies consisting of the complementarity-determining regions in the light chain (L chain) variable region and the heavy chain (H chain) variable region of a mouse monoclonal antibody against human tissue factor transferred into a human antibody, and reported that these could be expected as excellent therapeutic agents for DIC, arterial thrombosis and venous thrombosis (WO99/51743, WO01/24626). Especially preferred are humanized anti-human tissue factor antibodies comprising a combination of humanized H chain version i and humanized L chain version b2 described in WO99/51743, which are recombinant antibodies produced by CHO cells. Many anti-human tissue factor antibodies have already been reported (WO99/51743, WO88/07543, WO96/40921, WO98/40408, WO01/70984). They can be prepared by methods known to those skilled in the art because their antigen tissue factor has already been known (Ito T et al., J. Biochem. 114, 691-696, (1993)). These anti-human tissue factor antibodies are also preferred antibodies for use in the present invention.

Antibodies contained in formulations of the present invention may belong to any immunoglobulin class, preferably IgG such as IgG1, IgG2, IgG3 and IgG4.

As used herein, "antibody-containing solution" may be a solution containing any antibody, whether biologically derived or recombinant, preferably a culture medium in which mammalian cells such as CHO cells containing an antibody have been cultured, or a solution obtained by subjecting such a medium to a given treatment such as partial purification (bulk solution), or the solution formulation prepared for administration to animals such as humans as defined above.

As used herein, "foreign insoluble matters" mean the readily detectable foreign insoluble matters from which solution formulations must be free and clear when observed in containers with unaided eyes at a position of light intensity of approximately 1000 luxes under an incandescent lamp as defined in the section of Foreign Insoluble Matter Test for Injections in the part of General Tests, Processes and Apparatus in the Japanese Pharmacopoeia.

As used herein, "the biological activity of the antibody" means the antibody's ability to bind to its antigen, and can be determined by antigen-neutralizing activity assays. Formulations retaining the biological activity of the antibody mean that they retain 60% or more, preferably 70% or more, still more preferably 80% or more, most preferably 90% or more of the biological activity of the antibody stock after accelerated testing at 25° C. for 6 months when the antibody is a humanized anti-human tissue factor antibody.

In the present invention, purity tests of antibody formulations can be performed by gel filtration chromatography and anion-exchange chromatography described below.

In protein-containing formulations of the present invention, a high biological activity can be maintained without causing oxidation of the proteins in the absence of antioxidants and the formation of foreign insoluble matters can be inhibited in the protein-containing formulations by adding a poloxamer as a surfactant.

Poloxamers are nonionic surfactants consisting of a series of block copolymers of ethylene oxides and propylene oxides of the general formula below:

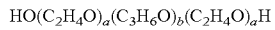

$$HO(C_2H_4O)_a(C_3H_6O)_b(C_2H_4O)_aH$$

Poloxamers include poloxamers 124, 188, 237, 338 and 407 described in USP (US Pharmacopoeia), among which poloxamer 188 is especially preferred in the present invention. Poloxamer 188 described in USP is a compound of the formula above wherein a is 80, b is 27, with an average molecular weight of 7680-9510, and poloxamer 188 described in BP (British Pharmacopoeia) is a compound of the formula above wherein a is about 75, b is about 30, with an average molecular weight of 8350. In addition, EP (European Pharmacopoeia) describes poloxamers 182, 184 and 331. Pluronics (trademark for poloxamers available from BASF) such as Pluronics L35, L43, L44, L61, L62, L64, F68, L81, P84, P85, F87, F88, L92, F98, L101, P103, P104, P105, F108, L121, P123 and F127 are also included in poloxamers in the present invention.

Poloxamers have previously been used as emulsifiers for fat emulsion preparations for intravenous injection or solubilizers for keeping the clarity of elixirs or syrups in pharmaceutical formulations, but have not been used as stabilizers for protein-containing formulations.

The amount of poloxamers to be added depends on the types of the poloxamers used and the concentration and type of the protein, but the amount of poloxamer 188 is typically 0.001-100 mg/mL, preferably 0.005-50 mg/mL, more preferably 0.01-10 mg/mL.

In protein-containing formulations of the present invention, the use of a poloxamer as a surfactant eliminates the need for adding antioxidants such as L-methionine as required when polysorbates were used.

Protein-containing formulations of the present invention may contain amino acids as stabilizers. The amino acids include, but not limited to, leucine, tryptophan, serine, glutamic acid, arginine, histidine and lysine and salts thereof.

In order to inhibit the formation of dimers during freeze/thaw cycles, formulations of the present invention may further contain sugar alcohols such as mannitol and sorbitol; and nonreducing oligosaccharides, e.g. nonreducing disaccharides such as sucrose and trehalose or nonreducing trisaccharides such as raffinose. Especially, nonreducing oligosaccharides are preferred. Preferred nonreducing oligosaccharides are nonreducing disaccharides, more preferably sucrose and trehalose.

Preferably, antibody-containing solution formulations of the present invention are substantially free from proteins such as human serum albumin or purified gelatin as stabilizers.

Antibody formulations of the present invention preferably have a pH of 4-8, more preferably 5-7.5. However, the pH depends on the antibody contained and is not limited to these values.

Formulations of the present invention may further contain isotonizing agents, e.g., polyethylene glycol; and sugars such as dextran, mannitol, sorbitol, inositol, glucose, fructose, lactose, xylose, mannose, maltose, sucrose, trehalose and raffinose.

Antibody-containing solution formulations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate. Other common additives may also be contained, e.g., inorganic salts such as sodium chloride, potassium chloride, calcium chloride, sodium phosphate, potassium phosphate and sodium bicarbonate; and organic salts such as sodium citrate, potassium citrate and sodium acetate.

Formulations of the present invention can be prepared by dissolving these components in an aqueous buffer known in the field of solution formulations such as a phosphate buffer (preferably sodium monohydrogen phosphate-sodium dihydrogen phosphate system) and/or a citrate buffer (preferably sodium citrate buffer) to prepare a solution formulation. The concentration of the buffer is typically 1-500 mM, preferably 5-100 mM, more preferably 10-50 mM.

Antibody-containing solution formulations of the present invention are normally administered via parenteral routes such as injection (e.g. subcutaneous, intravenous, intramuscular or intraperitoneal injection) or percutaneous, mucosal, nasal or pulmonary administration, but may also be orally administered.

Protein-containing formulations of the present invention may be either lyophilized formulations or solution formulations, preferably solution formulations. Solution formulations can be normally supplied in sealed and sterilized plastic or glass containers having a defined volume such as vials, ampules or syringes or a large volume such as bottles. In terms of convenience, prefilled syringes are preferred.

The amount of antibodies contained in formulations of the present invention is typically 0.1-200 mg/ml, preferably 1-120 mg/ml, depending on the type of the disease to be treated, the severity of the disease, the age of the patient and other factors.

As shown in the examples below, solution formulations of the present invention can retain the biological activity of the antibody formulations at a high level without adding antioxidants and inhibit the formation of foreign insoluble matters by adding a poloxamer as a surfactant.

The following examples further illustrate the present invention without, however, limiting the scope of the invention thereto. Various changes and modifications can be made by those skilled in the art in the light of the description herein, and such changes and modifications are also included in the present invention.

EXAMPLES

Samples
1. Antibody Sample
A humanized anti-human tissue factor antibody comprising a combination of humanized H chain version i and humanized L chain version b2 described in WO99/51743 was used as an anti-human tissue factor antibody. The anti-human tissue factor antibody used in the examples below is a recombinant antibody produced by CHO cells and belonging to the IgG4 class.

2. Granulocyte Colony-Stimulating Factor (G-CSF)

The granulocyte colony-stimulating factor used was produced by a genetic engineering technique in Chinese Hamster Ovary (CHO) cells using a gene recombination method and extracted and isolated/purified.

3. Parathyroid Hormone (PTH)

Parathyroid hormone having 1-84 residues was prepared by the method described in WO9014415.

Test Methods (1) TF-Neutralizing Activity Assay

Tissue factor (TF) is a blood coagulation factor VII receptor expressed on cell surfaces and has been positioned as a substantial trigger of the blood coagulation reaction. Tissue factor activates blood coagulation factors IX and X via formation of a complex with blood coagulation factor VII. Thus, the biological activity of humanized anti-human tissue factor antibodies can be assayed by the method described below using a blood coagulation factor VIIa solution and a blood coagulation factor X solution.

1. The following solutions were prepared.
1) A.B. (Assay Buffer): TBS (pH 7.6) containing 5 mmol/L $CaCl_2$, 0.1% BSA.
2) Mixed solution of Factor VIIa & Thromborel S: Factor VIIa and Thromborel S were diluted with A.B. to 0.1 PEU/mL and 0.42 mg/mL, respectively.
3) Factor X solution: Factor X was diluted with A.B. to 0.25 PEU/mL.
4) Mixed Testzyme chromogenic substrate S-2222 solution: A 1.5 mg/mL chromogenic substrate S-2222 solution was mixed with water and an aqueous polybrene solution in a ratio of 1:1:2.

2. The mixed solution of factor VIIa & Thromborel S was dispensed into a plate at 60 μL/well and allowed to stand at room temperature for 60 minutes.

3. The anti-human tissue factor antibody stock solution (standard solution) and sample solutions diluted with Factor X solution were dispensed into the plate at 40 μL/well and allowed to stand at room temperature for 30 minutes.

4. The reaction was stopped by adding 10 μL/well of a 0.5 mol/L EDTA solution, and then the mixed Testzyme chromogenic substrate S-2222 solution was dispensed into the plate at 50 μL/well and allowed to stand at room temperature for 30 minutes.

5. The absorbance at 405 nm-655 nm was measured.

6. The biological activity of each test sample was calculated as a percentage of the value of the standard solution based on calibration curve analysis.

Abbreviations

TBS: Tris Buffered Saline
BSA: Bovine Serum Albumin
EDTA: Ethylenediamine Tetraacetic Acid (2) Ion-Exchange Chromatography (IEC)

Assay conditions were as follows.
Column: DEAE-NPR (4.6 mm I.D.×3.5 cm)
Mobile Phase:
   A: 50 mmol/L Tris buffer, pH 8.0
   B: 50 mmol/L Tris buffer+500 mmol/L NaCl, pH 8.0
Gradient:
   0-5 min Solution B 0%
   5-40 min Solution B 0→50%
Flow rate: 1.0 mL/min
Detection: UV absorption at 280 nm
Sample load: equivalent to 100 μg (3) Analysis of Foreign Insoluble Matters Solution formulations in containers were observed with unaided eyes at a position of light intensity of approximately 1000 luxes under an incandescent lamp as defined in the section of Foreign Insoluble Matter Test for Injections in the part of General Tests, Processes and Apparatus in the Japanese Pharmacopoeia.

Example 1: Effects of Adding Surfactants on Biological Activity

Changes over time in the biological activity of anti-human tissue factor antibody solution formulations containing various surfactants were tested. Samples (pH 6.0) containing 2.3 mg/mL of the anti-human tissue factor antibody in an acetate buffer and 0.5 mg/mL of polysorbate 20 or 80 (both manufactured by company A) or poloxamer 188 (manufactured by company B) as a surfactant were tested for biological activity (TF-neutralizing activity) after storage at 5° C. for 14 days and at 40° C. for 14 days. A group containing no surfactant was also tested in the same manner for comparison. The results are shown in FIG. 1.

In contrast to the formulation containing polysorbate 80, which showed a marked loss in the biological activity of the anti-human tissue factor antibody, the formulation containing poloxamer 188 retained a comparable activity to that of the formulation containing no surfactant. An activity loss was also observed in the formulation containing polysorbate 20 known as an injectable surfactant in the field.

Example 2: Effects of Surfactants on Biological Activity and Purity

Figure 2:
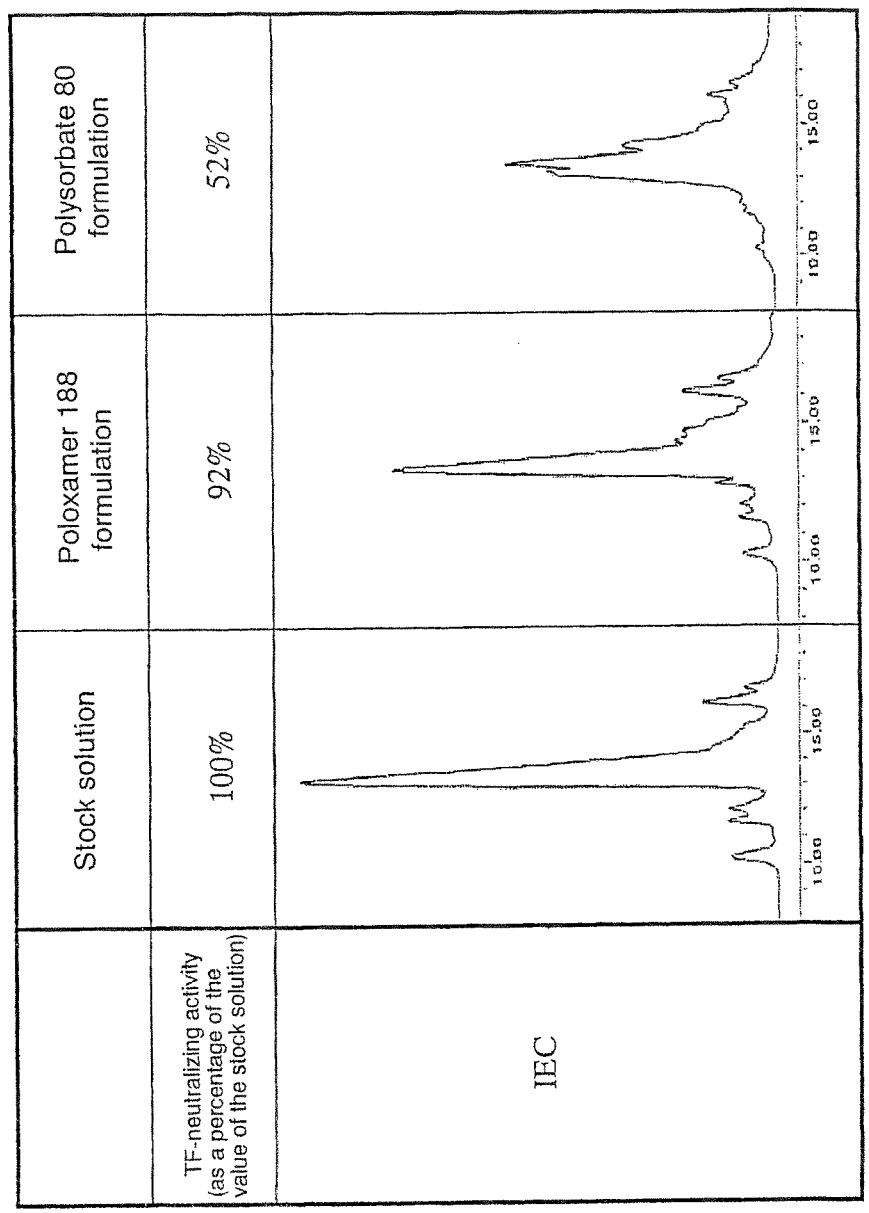
FIG. 2 represents anion-exchange chromatograms of anti-human tissue factor antibody solution formulations containing poloxamer 188 or polysorbate 80.

The effects of adding surfactants on the biological activity and purity of anti-human tissue factor antibody solution formulations were tested. Samples (pH 5.5) containing 10 mg/mL of the anti-human tissue factor antibody in an acetate buffer and 0.5 mg/mL of polysorbate 80 (manufactured by company C) or poloxamer 188 (manufactured by company D) as a surfactant were tested for biological activity by the TF-neutralizing activity assay and for purity by ion-exchange chromatography (IEC) after accelerated testing at 25° C. for 6 months. The anti-human tissue factor antibody stock solution (bulk) without accelerated testing was also tested in the same manner for comparison. The results are shown in FIG. 2.

The biological activity of the formulation containing poloxamer 188 was 92% of the biological activity of the anti-human tissue factor antibody stock solution, while the biological activity of the formulation containing polysorbate 80 was 52%.

In ion-exchange chromatography, the main peak dropped and a new peak (indicated by an arrow in FIG. 2) appeared immediately before the main peak in the anti-human tissue factor antibody solution formulation containing polysorbate 80. The peak fraction appearing immediately before the main peak was attributed to a derivative containing some oxidized amino acid residues. However, the formulation containing poloxamer 188 retained a chromatogram similar to that of the anti-human tissue factor antibody stock solution.

These results showed that poloxamer 188 is superior to polysorbate 80 in both biological activity and purity.

Example 3: Effect of Adding L-Methionine on the Activity Loss Induced by Polysorbate 80 in the Anti-Human Tissue Factor Antibody as Compared with the Effect of Adding a Poloxamer The effect of adding L-methionine on the activity loss induced by polysorbate 80 in the anti-human tissue factor antibody solution formulation was tested and compared with the formulation containing poloxamer 188. Samples (pH 5.5) containing 10 mg/mL of the anti-human tissue factor antibody in an acetate buffer and
1) 0.5 mg/mL of polysorbate 80,
2) 0.5 mg/mL of polysorbate 80 plus 5 mg/mL of L-methionine, or
3) 0.5 mg/mL of poloxamer 188
were prepared.

Each sample was tested for biological activity by the TF-neutralizing activity assay after accelerated testing at 25° C. for 6 months, and compared with the biological activity of the anti-human tissue factor antibody stock solution (bulk).

Figure 3:
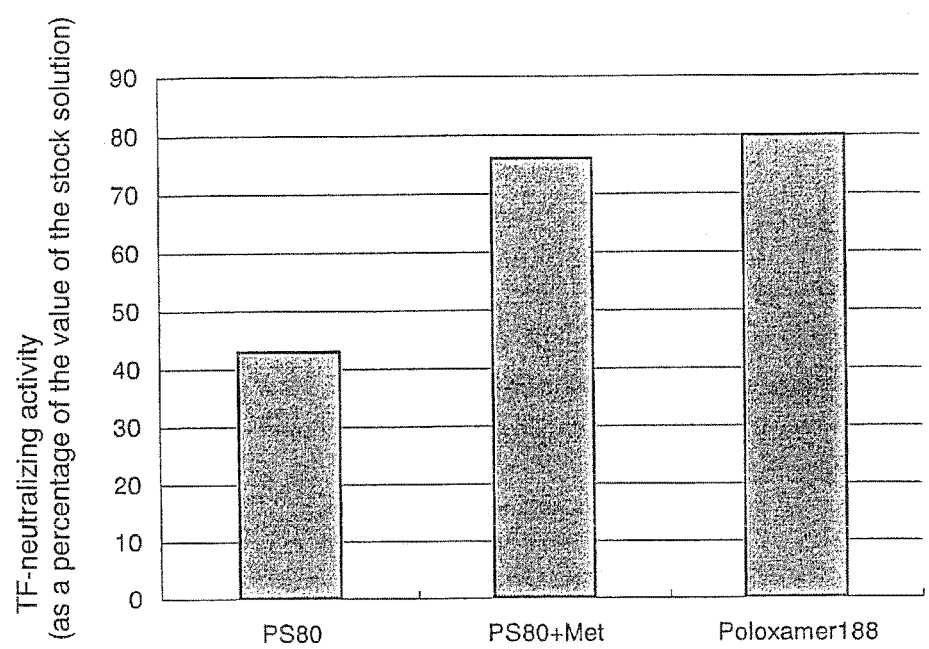
FIG. 3 shows the effect of adding L-methionine on the activity loss induced by polysorbate 80 in an anti-human tissue factor antibody as compared with the effect of adding a poloxamer.

The results are shown in FIG. 3. The activity loss induced by polysorbate 80 was inhibited by adding L-methionine. The sample containing poloxamer 188 showed a biological activity comparable to or higher than that of the sample containing polysorbate 80 and L-methionine.

Example 4: Effects of Surfactants on Foreign Insoluble Matters

The effects of adding surfactants on the formation of foreign insoluble matters in anti-human tissue factor antibody solution formulations were tested. Samples (pH 6.0) containing 10 mg/mL of the anti-human tissue factor antibody in an acetate buffer and 0.5 mg/mL of polysorbate 80 (manufactured by company C) or poloxamer 188 (manufactured by company D) as a surfactant were tested for foreign insoluble matters immediately after preparation and after storage at 5° C. for 24 months. A group containing no surfactant was also tested in the same manner for comparison. The results are shown in Table 1. The number of vials in which foreign insoluble matters were observed among 5 sample vials was shown. Insoluble matters were visually observed immediately after preparation in the sample containing no surfactant. However, no formation of foreign insoluble matters was observed in the samples containing poloxamer 188 and polysorbate 80.

TABLE 1

| Surfactant | None | Poloxamer 188 | polysorbate 80 |
|---|---|---|---|
| Initial | 5/5 | 0/5 | 0/5 |
| 5° C.-24M | 5/5 | 0/5 | 0/5 |

(4) Experiment on the Stabilization of the Protein by a Poloxamer

Various surfactants were added to the granulocyte colony-stimulating factor solution formulation and parathyroid hormone solution formulation described above to evaluate their effects on the oxidation of granulocyte colony-stimulating factor and parathyroid hormone.

Example 5: Influences of Surfactants on the Oxidation of Granulocyte Colony-Stimulating Factor The influences of surfactants on granulocyte colony-stimulating factor solution formulations were tested. Samples (pH 6.5) containing 0.25 mg/mL of colony-stimulating factor in a phosphate buffer and 0.05% of polysorbate 80 (manufactured by company A), polysorbate 20 (manufactured by company A), or poloxamer 188 (manufactured by company B) as a surfactant were tested for the content of oxidized derivatives of granulocyte colony-stimulating factor by reverse-phase chromatography (RPC) after accelerated testing at 25° C. for 5 weeks.

Figure 4:
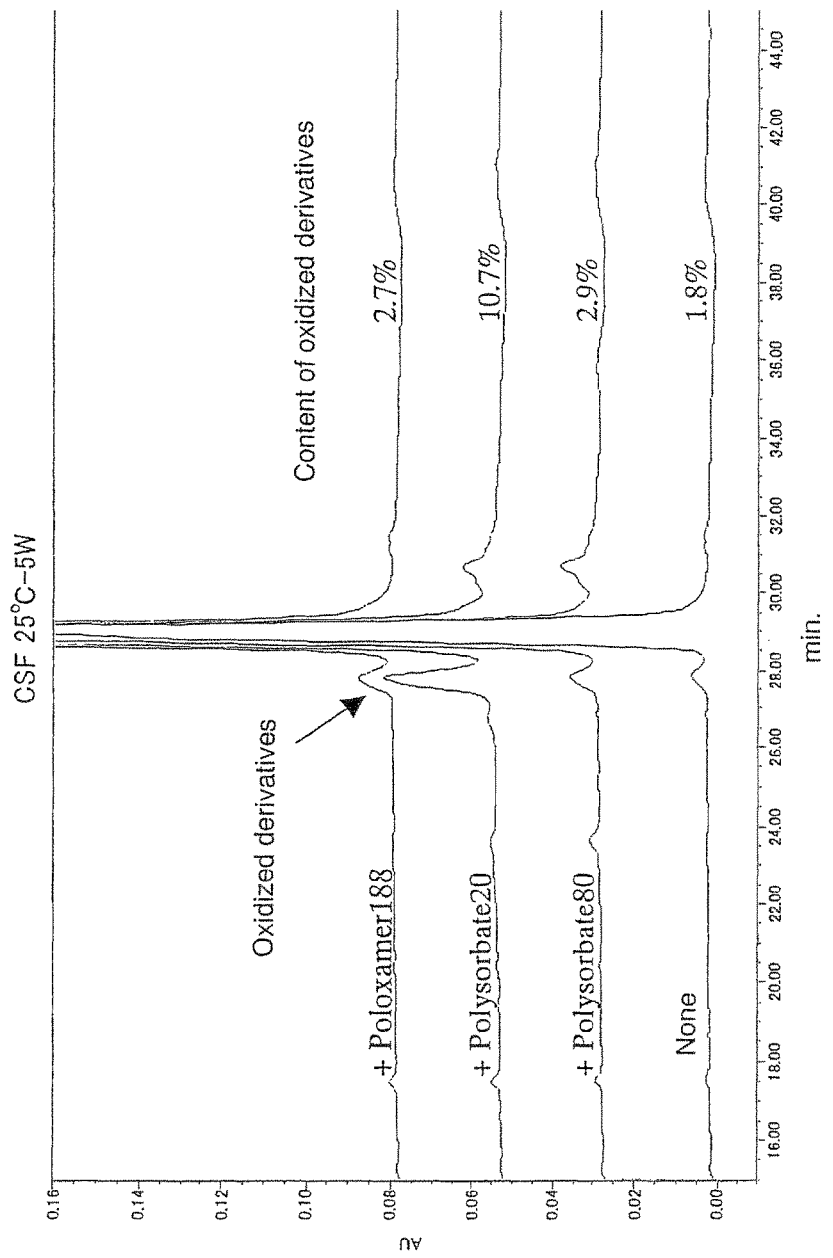
FIG. 4 represents chromatograms showing the influence of polysorbate 80, polysorbate 20 or poloxamer 188 on the oxidation of granulocyte colony-stimulating factor.

Assay conditions were as follows.
Column: DAISOPAK SP-300-5-C4-P (4.6 mm I.D.×25 cm)
Mobile Phase:
　A acetonitrile:water:trifluoroacetic acid=400:600:1
　B acetonitrile:water:trifluoroacetic acid=800:200:1
Gradient:
　0-25 min Solution B 20→90%
　25-40 min Solution B 90→90%
　40-41 min Solution B 90→20%
　41-60 min Solution B 20%
Flow rate: 0.3 mL/min
Load: 10 μL
Column temperature: 35° C.
Detection wavelength: UV absorption at 215 nm
The results are shown in FIG. 4.

Reverse-phase chromatography showed that oxidized derivatives (indicated by an arrow in FIG. 4) appeared immediately before the main peaks of the granulocyte colony-stimulating factor solution formulations containing various surfactants. These peak fractions were attributed to derivatives of granulocyte colony-stimulating factor containing some oxidized amino acid residues.

The content of oxidized derivatives was the highest in the sample containing polysorbate 20, followed by polysorbate 80 and then poloxamer 188.

Example 6: Influences of Surfactants on the Oxidation of Parathyroid Hormone

The influences of surfactants on parathyroid hormone solution formulations were tested. Samples (pH 5.0) containing 0.25 mg/mL of parathyroid hormone in a citrate buffer and 0.05% of polysorbate 80 (manufactured by company A), polysorbate 20 (manufactured by company A), or poloxamer 188 (manufactured by company B) as a surfactant were tested for the content of oxidized derivatives of parathyroid hormone by reverse-phase chromatography (RPC) after accelerated testing at 40° C. for 2 weeks.

Figure 5:
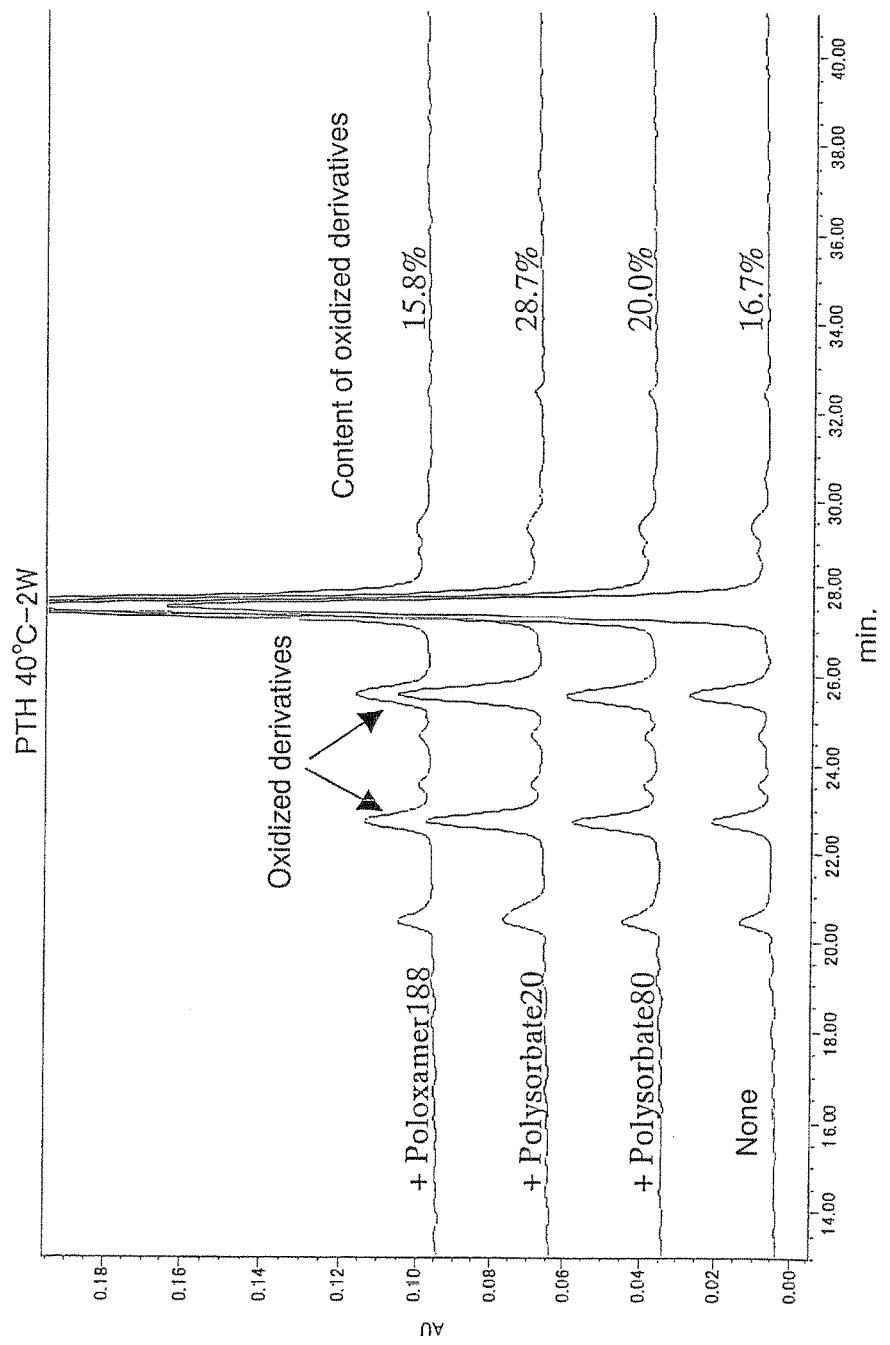
FIG. 5 represents chromatograms showing the influence of polysorbate 80, polysorbate 20 or poloxamer 188 on the oxidation of parathyroid hormone.

Assay conditions were as follows.
Column: YMC-Pack ODS A-312 (4.6 mm I.D.×15 cm)
Mobile Phase:
　A acetonitrile:water:trifluoroacetic acid=0:1000:1
　B acetonitrile:water:trifluoroacetic acid=600:400:1
Gradient:
　0-40 min Solution B 40→60%
　40-42 min Solution B 60→60%
　42-42.5 min Solution B 60→40%
　42.5-60 min Solution B 40%
Flow rate: 1.0 mL/min
Load: 10 μL
Column temperature: 25° C.
Detection wavelength: UV absorption at 215 nm
The results are shown in FIG. 5.

Reverse-phase chromatography showed that oxidized derivatives (indicated by arrows in FIG. 5) appeared immediately before the main peaks of the parathyroid hormone solution formulations containing various surfactants. These peak fractions were attributed to derivatives of parathyroid hormone containing some oxidized amino acid residues.

The content of oxidized derivatives was the highest in the sample containing polysorbate 20, followed by polysorbate 80 and then poloxamer 188.

These results showed that poloxamer 188 is superior to polysorbates in the antioxidant effect on protein solution formulations.

INDUSTRIAL APPLICABILITY

Stabilized protein-containing formulations of the present invention show neither biological activity loss nor formation of foreign insoluble matters even after long-term storage. They are stable formulations in which the generation of oxidized derivatives of proteins is effectively inhibited.

What is claimed is:

1. A method for inhibiting the oxidation of a protein in a protein formulation and for inhibiting the formation of foreign insoluble matters in said protein formulation, the method comprising adding a poloxamer as a surfactant into the protein formulation, wherein said protein is granulocyte colony-stimulating factor (G-CSF) having a sugar chain and obtained by expression in Chinese hamster ovary (CHO) cells, wherein said protein formulation does not contain an antioxidant, wherein said protein formulation, after such addition, consists of G-CSF, a poloxamer, a buffer, and optionally one or more free amino acids, wherein the poloxamer is poloxamer 188 at a concentration in a range of 0.01-10 mg/mL, and wherein oxidation of said protein is inhibited during storage at 25° C. for 5 weeks.

2. The method of claim 1 in which the buffer is phosphate, acetate or citrate buffer.

3. The method of claim 1 in which the buffer is acetate buffer.

4. The method of claim 1 in which the formulation includes one or more free amino acids.

5. The method of claim 1 in which the formulation does not include one or more free amino acids.

* * * * *